US011134910B2

(12) United States Patent
Kim

(10) Patent No.: US 11,134,910 B2
(45) Date of Patent: Oct. 5, 2021

(54) MAMMOGRAPHY DEVICE COMPRISING MULTIPLE SENSORS ON A FRONT SIDE OF A MAMMOGRAPHY PLATE CAPABLE OF RECOGNIZING TARGET PERSON

(71) Applicant: Vieworks Co., Ltd., Anyang-si (KR)

(72) Inventor: Seok Jong Kim, Namyangju-si (KR)

(73) Assignee: VIEWORKS CO., LTD., Anyang-si (KR)

( * ) Notice: Subject to any disclaimer, the term of this patent is extended or adjusted under 35 U.S.C. 154(b) by 0 days.

(21) Appl. No.: 16/526,301

(22) Filed: Jul. 30, 2019

(65) Prior Publication Data

US 2020/0037971 A1 Feb. 6, 2020

(30) Foreign Application Priority Data

Aug. 3, 2018 (KR) .................. 10-2018-0090769

(51) Int. Cl.
*A61B 6/00* (2006.01)
*A61B 6/02* (2006.01)
(Continued)

(52) U.S. Cl.
CPC .............. *A61B 6/502* (2013.01); *A61B 6/025* (2013.01); *A61B 6/04* (2013.01); *A61B 6/0407* (2013.01);
(Continued)

(58) Field of Classification Search
CPC .......... A61L 6/025; A61L 6/04; A61L 6/0407; A61L 6/0414; A61L 6/0421; A61L 6/10;
(Continued)

(56) References Cited

U.S. PATENT DOCUMENTS 6,674,835 B2 * 1/2004 Kaufhold ............. A61B 5/4869
378/53
6,751,285 B2 * 6/2004 Eberhard ............... A61B 6/502
378/37
(Continued)

FOREIGN PATENT DOCUMENTS

JP 2012-019842 A 2/2012
JP 2015-058053 A 3/2015
(Continued)

OTHER PUBLICATIONS

An English translation of JP2015-058053A by Patent Translate.*
An English translation of JP2012-019842A by Patent Translate.*
Extended European Search Report dated Dec. 17, 2019.

*Primary Examiner* — Allen C. Ho
(74) *Attorney, Agent, or Firm* — Rabin & Berdo, P.C.

(57) ABSTRACT

Disclosed is a mammography device capable of recognizing a target person, the mammography device including: a body unit; an arm frame connected to the body unit, and rotating in a clockwise or counterclockwise direction; an X-ray generator placed at a top of the arm frame, and emitting X-rays; a mammography plate provided at a position corresponding to the X-ray generator, and obtaining an X-ray image of a breast of a target person; a compression unit placed between the X-ray generator and the mammography plate, and moving vertically to compress a target part; a sensor unit placed inside the mammography plate, and detecting whether the target person is present; and a control unit controlling an operation of the arm frame on the basis of whether the target person is detected by the sensor unit. Accordingly, a safety accident that may occur in a mammography process using the mammography device is reduced.

9 Claims, 9 Drawing Sheets

(51) Int. Cl.
  *A61B 6/04* (2006.01)
  *A61B 6/10* (2006.01)
  *G01D 5/24* (2006.01)

(52) U.S. Cl.
  CPC .......... *A61B 6/0414* (2013.01); *A61B 6/0421* (2013.01); *A61B 6/10* (2013.01); *A61B 6/102* (2013.01); *A61B 6/4208* (2013.01); *A61B 6/44* (2013.01); *A61B 6/4429* (2013.01); *A61B 6/4435* (2013.01); *A61B 6/4441* (2013.01); *A61B 6/4447* (2013.01); *A61B 6/4458* (2013.01); *A61B 6/54* (2013.01); *A61B 6/542* (2013.01); *A61B 6/545* (2013.01); *G01D 5/24* (2013.01)

(58) Field of Classification Search
  CPC ... A61L 6/102; A61L 6/40; A61L 6/42; A61L 6/4208; A61L 6/44; A61L 6/4429; A61L 6/4435; A61L 6/4441; A61L 6/4447; A61L 6/4458; A61L 6/502; A61L 6/542; A61L 6/545
  USPC .......... 378/22, 26, 37, 62, 91, 196–198, 189, 378/208, 209
  See application file for complete search history.

(56) References Cited

U.S. PATENT DOCUMENTS

| | | | | |
|---|---|---|---|---|
| 7,149,335 B2* | 12/2006 | Kaufhold | ................ | G06T 5/008 382/132 |
| 7,319,735 B2 | 1/2008 | Defreitas et al. | | |
| 7,327,826 B2* | 2/2008 | Hanke | ..................... | A61B 6/06 378/155 |
| 7,463,713 B2* | 12/2008 | Mertelmeier | .......... | A61B 6/025 378/22 |
| 7,496,176 B2* | 2/2009 | Aslund | .................. | A61B 6/542 378/96 |
| 7,515,682 B2* | 4/2009 | Li | ......................... | A61B 6/025 378/210 |
| 7,558,366 B2* | 7/2009 | Barth | .................... | G06T 11/006 378/197 |
| 7,639,779 B2* | 12/2009 | Kashiwagi | ............. | A61B 6/502 378/165 |
| 7,693,254 B2* | 4/2010 | Muller | .................. | G06T 11/008 378/37 |
| 7,697,661 B2* | 4/2010 | Souchay | ................ | A61B 6/542 378/37 |
| 7,853,064 B2* | 12/2010 | Bernard | ................ | G06T 11/008 382/132 |
| 7,881,513 B2* | 2/2011 | Bernard | ................ | G06T 7/0012 382/128 |
| 8,041,094 B2* | 10/2011 | Bernard | ................ | G06T 7/0012 382/131 |
| 8,903,039 B2* | 12/2014 | Masumoto | ........... | A61B 6/5205 378/21 |
| 9,414,801 B2* | 8/2016 | Kim | ....................... | A61B 6/545 |
| 9,451,923 B2* | 9/2016 | Hemmendorff | ........ | A61B 6/547 |
| 9,597,040 B2* | 3/2017 | Hemmendorff | ........ | A61B 6/502 |
| 9,743,895 B2* | 8/2017 | Ko | .......................... | A61B 6/502 |
| 9,743,997 B2* | 8/2017 | Grimbergen | .......... | A61B 6/0414 |
| 10,426,420 B2* | 10/2019 | Arai | ........................ | A61B 6/502 |
| 10,448,917 B2* | 10/2019 | Arai | ........................ | A61B 6/42 |
| 10,463,338 B2* | 11/2019 | Arai | ........................ | A61B 6/42 |
| 10,575,812 B2* | 3/2020 | Kobayashi | ............... | A61B 6/00 |
| 10,588,600 B2* | 3/2020 | Arai | ........................ | A61B 6/502 |
| 10,856,831 B2* | 12/2020 | Moon | .................... | A61B 6/467 |
| 11,058,372 B2* | 7/2021 | de Groot | ................. | A61B 6/54 |
| 2015/0245806 A1 | 9/2015 | Kim et al. | | |
| 2017/0367674 A1 | 12/2017 | Arai et al. | | |

FOREIGN PATENT DOCUMENTS

| | | |
|---|---|---|
| JP | 2017-012408 A | 1/2017 |
| JP | 2017-225502 A | 12/2017 |
| JP | 2017-225633 A | 12/2017 |
| KR | 10-1030459 B1 | 4/2011 |
| KR | 10-1136370 B1 | 4/2012 |
| KR | 10-2014-0118450 A | 10/2014 |

* cited by examiner

MAMMOGRAPHY DEVICE COMPRISING MULTIPLE SENSORS ON A FRONT SIDE OF A MAMMOGRAPHY PLATE CAPABLE OF RECOGNIZING TARGET PERSON

CROSS REFERENCE TO RELATED APPLICATION

The present application claims priority to Korean Patent Application No. 10-2018-0090769, filed Aug. 3, 2018, the entire contents of which is incorporated herein for all purposes by this reference.

BACKGROUND OF THE INVENTION

Field of the Invention

The present invention relates generally to a mammography device. More particularly, the present invention relates to a mammography device capable of recognizing a target person, wherein a sensor unit is placed in the front of a mammography plate to determine whether a target person is positioned at a front side of the mammography plate and a rotation speed and a vertically moving speed of an arm frame are reduced when it is determined by the sensor unit that the target person is positioned at the front side of the mammography plate, whereby a safety accident that may occur in a mammography process is reduced.

Description of the Related Art

Due to westernization of lifestyle, the incidence of breast cancer has been increased. Until now, the cause of breast cancer has not been clearly elucidated. Therefore, the best way to prevent breast cancer is early diagnosis through periodical examination.

In the related art, as a device for breast cancer diagnosis using an image, an X-ray mammography device, an ultrasonic scanner, a magnetic resonance imaging device, and the like have been used. Among the devices, the mammography device is the most commonly used device in periodical examination of health for early diagnosis of breast cancer.

The mammography device is a medical device capable of early diagnosis of breast cancer, wherein the breast, which is a target part, is fixed in a compressed manner and the target part is irradiated with X-rays. The X-rays passed through the target part are analyzed using a phenomenon that transmission coefficients of X-ray vary according to tissue and such that an internal image of the target part is obtained.

In order to conduct the breast cancer examination using the mammography device, the target person is positioned at a front side of a mammography plate according to instructions of the examiner, then i) craniocaudal (CC) mammography starting from the central top to the bottom of the left and the right breast and II) mediolateral oblique (MLO) mammography in an oblique direction of the left and the right breast are performed.

Particularly, in CC mammography, mammography is conducted on the center of the left and the right breast. On the other hand, in left mediolateral oblique (LMLO) and right medioletral oblique (RMLO) mammography, mammography is conducted in an oblique direction of the left and the right breast. When switching from CC mammography to MLO mammography, it is essential to rotate an arm frame of the mammography device in a clockwise direction or in a counterclockwise direction and to vertically move the arm frame for height adjustment.

In the conventional mammography device, even when the target person is in contact with the mammography plate for CC mammography and MLO mammography, the arm frame operates at the same speed as when the target person is not present in front of the mammography plate. Thus, it often happens that the target person is injured during the process where the arm frame rotates or vertically moves to change the mammography positioning or to finely adjust the position.

Therefore, in order to solve the problems of the conventional mammography device, a mammography device capable of reducing the occurrence of safety accidents during the mammography preparation process is required.

The foregoing is intended merely to aid in the understanding of the background of the present invention, and is not intended to mean that the present invention falls within the purview of the related art that is already known to those skilled in the art.

Document of Related Art (Patent Document 1) U.S. Pat. No. 7,319,735, "MAMMOGRAPHY SYSTEM AND METHOD EMPLOYING OFFSET COMPRESSION PADDLES, AUTOMATIC COLLIMATION, AND RETRACTABLE ANTI-SCATTER GRID"

SUMMARY OF THE INVENTION

Accordingly, the present invention has been made keeping in mind the above problems occurring in the related art, and the present invention is intended to propose a mammography device wherein a sensor unit is placed in the front of a mammography plate to determine whether the target person is positioned at a front side of the mammography plate and a rotation speed and a vertically moving speed of an arm frame are adjusted when it is determined that the target person is present, whereby an safety accident that may occur in a mammography process via the mammography device is reduced.

It is to be understood that technical problems to be solved by the present invention are not limited to the aforementioned technical problems and other technical problems which are not mentioned will be apparent from the following description to a person with an ordinary skill in the art to which the present invention pertains.

In order to achieve the above object, according to an embodiment of the present invention, there is provided a mammography device including: a body unit; an arm frame connected to the body unit, and rotating in a clockwise direction or in a counterclockwise direction; an X-ray generator placed at a top of the arm frame, and emitting X-rays; a mammography plate provided at a position corresponding to the X-ray generator, and obtaining an X-ray image of a breast of a target person; a compression unit placed between the X-ray generator and the mammography plate, and moving vertically to compress a target part; a sensor unit placed inside the mammography plate, and detecting whether the target person is present; and a control unit controlling an operation of the arm frame on the basis of whether the target person is detected by the sensor unit.

Here, the sensor unit may include: multiple sensors placed on a front side of the mammography plate; and a sensor substrate on which the multiple sensors are arranged.

The multiple sensors may be capacitive touch sensors.

Here, the multiple sensors may be arranged at regular intervals on the sensor substrate.

Further, the sensor unit may determine that the target person is positioned at the front side of the mammography plate, when a detection signal is generated by a preset number of sensors or more among the multiple sensors.

Furthermore, the sensor unit may further include one or more gaskets arranged between the front side of the mammography plate and the sensor substrate.

Here, the gaskets may be arranged at positions corresponding to the sensors arranged on the sensor substrate.

Further, the control unit of the mammography device of the present invention reduces, when the target person is detected by the sensor unit, a rotation speed of the arm frame to a first set value or less, or a vertically moving speed of the arm frame to a second set value or less.

The mammography device of the present invention is provided with a sensor unit in the front of the mammography plate to determine whether the target person is positioned in front of the mammography device for mammography, and when it is determined that the target person is positioned at the front side of the mammography plate, the operation speed of the arm frame is reduced such that an safety accident that may occur in the operation process of the arm frame is prevented.

Further, the mammography device of the present invention reduces the operation speed of the arm frame when the target person is positioned at the front side of the mammography plate, so that the examiner is capable of finely adjusting the position of the arm frame, thereby increasing usability of the mammography device.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Figure 1:
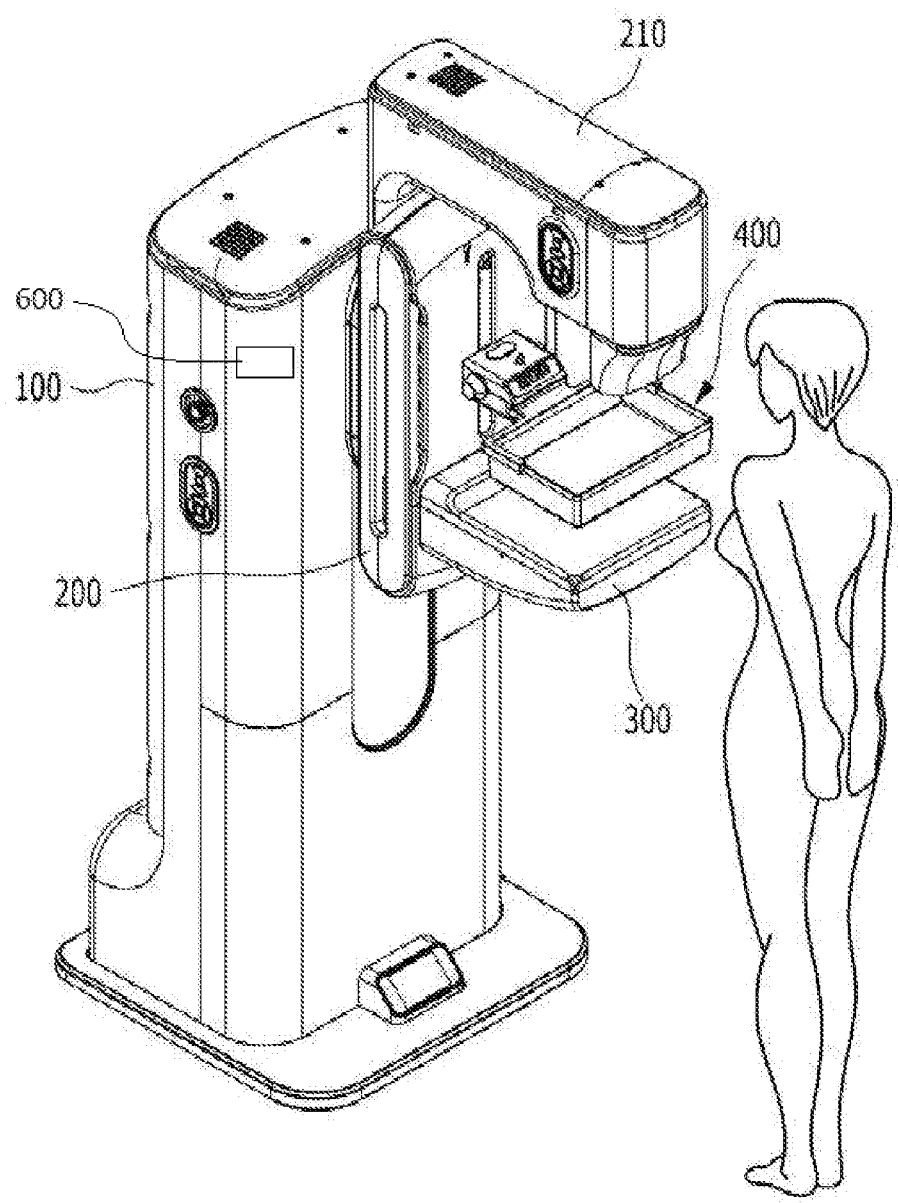
FIG. 1 is a perspective diagram illustrating a mammography device according to an embodiment of the present invention.

Hereinafter, the present invention will be described in detail with reference to the drawings. It is noted that the same reference numerals designate the same elements throughout the drawings. Further, a detailed description of known functions and configurations that make the subject matter of the present invention unclear will be omitted.

It will be understood that when an element is referred to as being coupled or connected to another element, it can be directly coupled or connected to the other element or intervening elements may be present therebetween. Further, throughout the specification, when a first member is placed "on" a second member, the first member is in contact with the second member or an intervening member is present therebween.

In the present specification, it will be understood that terms such as "including", "having", etc. are intended to indicate the existence of the features, numbers, steps, actions, elements, parts, or combinations thereof disclosed in the specification, and are not intended to preclude the possibility that one or more other features, numbers, steps, actions, elements, parts, or combinations thereof may exist or may be added.

Before describing a mammography device of the present invention, a mammography device will be briefly described with reference to FIGS. 1 and 2.

FIG. 1 is a perspective diagram illustrating a mammography device according to an embodiment of the present invention. FIG. 2 is a side diagram illustrating a mammography device according to an embodiment of the present invention and schematically illustrating internal elements of a mammography plate.

A mammography device schematically includes a body unit 100, an arm frame 200 combined with the body unit 100, and a mammography plate 300 and a compression unit 400 attached to a side of the arm frame 200.

First, the body unit 100 is a type of fixed frame and is combined with the arm frame 200 via a rotation shaft 110 to rotate the arm frame 200 in a clockwise direction or in a counterclockwise direction depending on mammography positioning.

Specifically, the body unit 100 is configured such that in the case of i) craniocaudal (CC) mammography, the arm frame 200 is positioned in parallel with the body unit 100; and in the case of II) left mediolateral oblique (LMLO) mammography, the arm frame 200 is rotated in a clockwise direction; and oppositely, in the case of iii) right mediolateral oblique (RMLO) mammography, the arm frame 200 is rotated in a counterclockwise direction, whereby the arm frame 200 is rotated depending on the mammography positioning.

Further, the body unit 100 vertically moves the arm frame 200 according to the chest level of a target person in such a manner that the breast of the target person is placed on a mammography plate 300 attached to the arm frame 200.

Next, the arm frame 200 is formed in a shape of Korean letter "ㄷ" when viewed from the side, and is a frame called a "C arm" or a "gantry" because of its specific shape.

Figure 2:
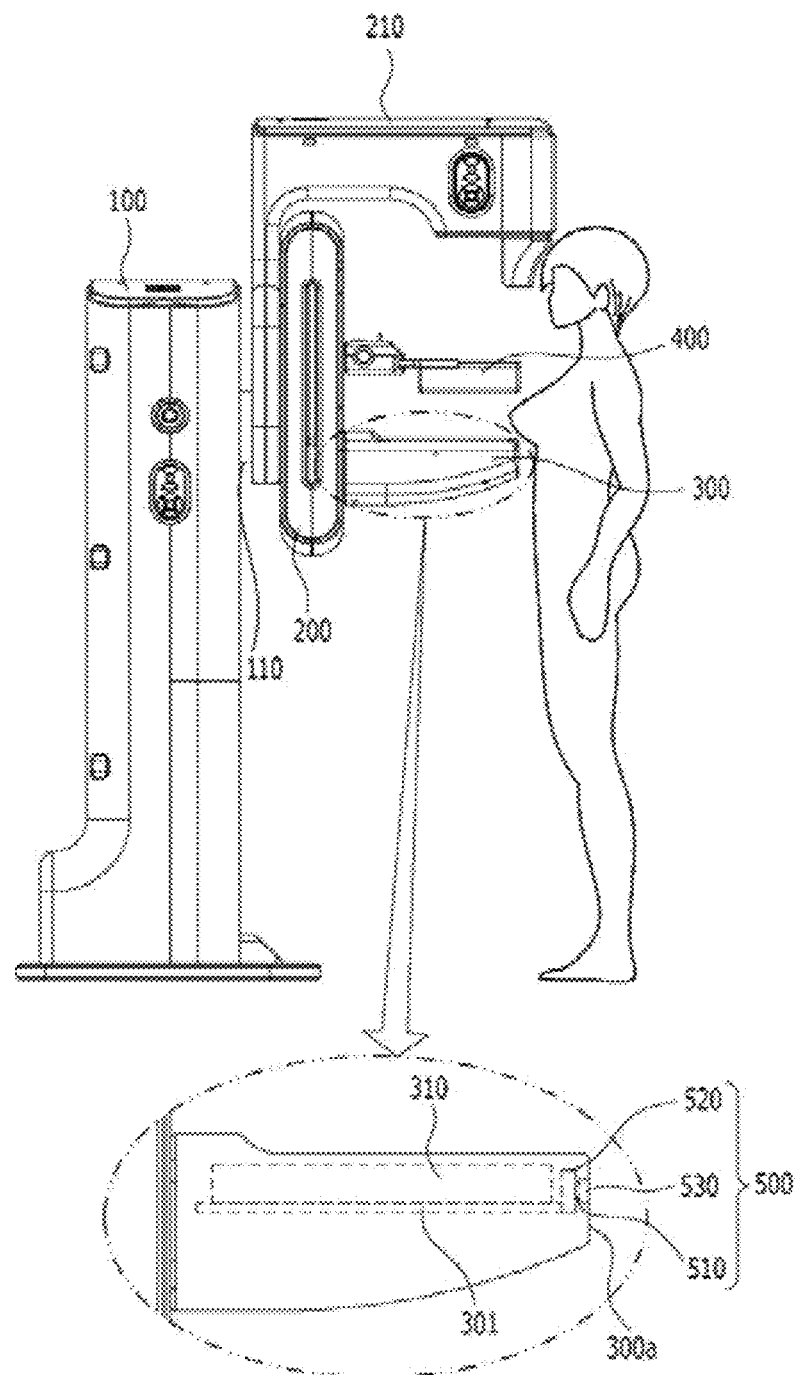
FIG. 2 is a side diagram illustrating a mammography device according to an embodiment of the present invention and schematically illustrating internal elements of a mammography plate.

As shown in FIGS. 1 and 2, to a side of the arm frame 200, the mammography plate 300 provided with the top on which a target part (breast) is placed, the compression unit 400 compressing the target part placed on the mammography plate 300, and the like are attached. At the top of the arm frame 200, placed is an X-ray generator 210 generating X-rays to irradiate the target part, by causing electrons having high kinetic energy to collide with a metal.

Here, the compression unit 400 compresses the target part to make the target part thin before the target part is irradiated with X-rays as briefly described above. The target part which is the breast is composed of soft tissue only. Thus, if the breast is not made to be thin by being compressed, the difference in X-ray attenuation coefficient between soft tissues is not large so that it is impossible to obtain a clear image. Further, when the soft tissues overlap, there may be a hidden lesion, which may decrease the precision of breast cancer diagnosis. Therefore, the mammography device is capable of enhancing the resolution of the image via the compression unit 400.

Further, the mammography plate 300 is provided with the top on which the target part is placed, and is provided with an X-ray detector 310 therein as shown in the enlarged view of FIG. 2. The X-ray detector 310 generates different electrical signals for the respective positions depending on the amount of incident X-rays that have passed through the target part, and generates, on the basis of electrical signals and position information generated by the X-ray detector 310, a tomogram of the target part (namely, an X-ray image of the breast of the target person).

Particularly, it is desired that the mammography plate 300 is provided at a position corresponding to the X-ray generator 210 placed at the top of the arm frame 200 so as to enhance resolution and precision of the X-ray image.

The conventionally proposed mammography device included only the body unit 100, the arm frame 200, the X-ray generator 210, the mammography plate 300, the compression unit 400, and the like. Thus, there was no means for checking whether the target person was positioned in front of the mammography device. Thus, when the examiner operated the arm frame 200 to change the mammography positioning or to finely adjust the position of the arm frame 200 without recognizing that target person was positioned in front of the mammography device, the target person could not avoid being injured by the rotating or vertically moving arm frame 200.

Thus, unlike the conventional mammography device, the mammography device of the present invention as shown in FIG. 2 further includes, inside the mammography plate 300: a sensor unit 500 detecting whether the target person is positioned in front of the mammography device; and a control unit 600 (see FIG. 1) controlling the operation of the arm frame 200 on the basis of the result of the detection by the sensor unit 500 to prevent a safety accident, whereby a safety accident that may occur during the mammography process is minimized.

Hereinafter, with reference to FIGS. 3 to 5, the sensor unit 500 of the mammography device according to an embodiment of the present invention, which is different from the conventional mammography device, and the control unit controlling the operation of the arm frame 200 on the basis of the result of the detection by the sensor unit 500 will be described in detail.

Figure 3:
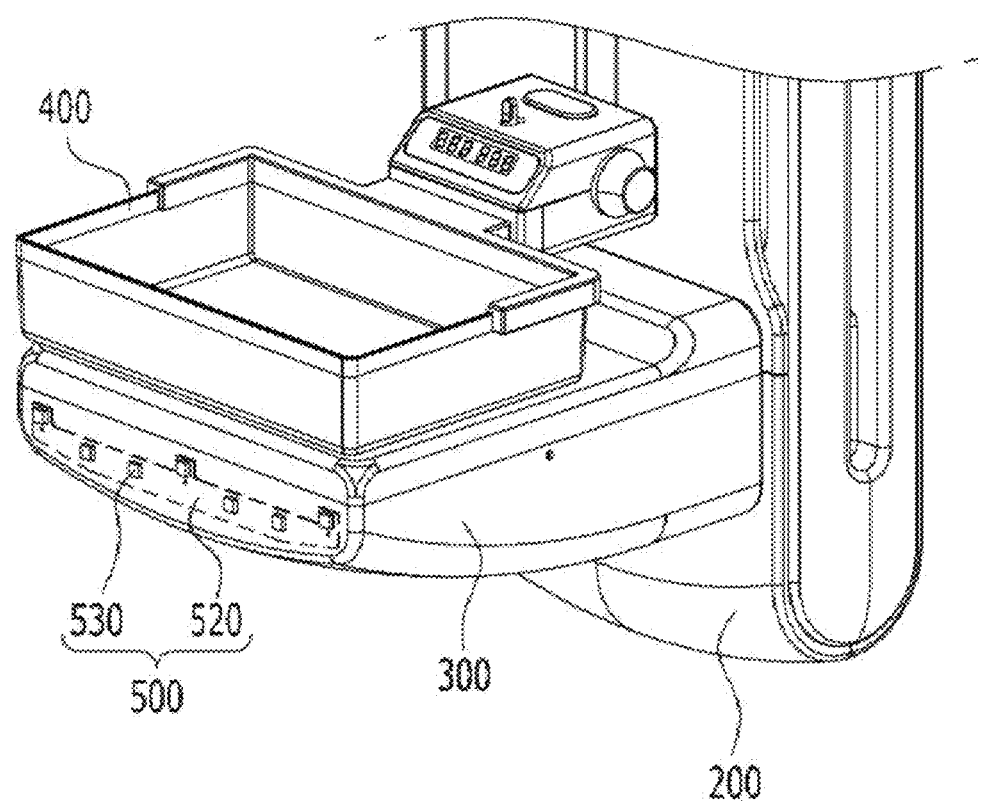
FIG. 3 is a perspective view illustrating a mammography plate and a compression unit of the present invention.

FIG. 3 is a perspective view illustrating a mammography plate 300 and a compression unit 400 of the present invention. FIG. 4 is an exploded diagram illustrating a sensor unit positioned inside a mammography plate 300 of the present invention. FIG. 5 is a flowchart illustrating an operation process of an arm frame 200 of a mammography device of the present invention depending on whether a target person is present.

As briefly described above, according to an embodiment of the present invention, like the conventional mammography device, the mammography device includes: the body unit 100; the arm frame 200 coupled to the body unit 100 and rotating in a clockwise direction or in a counterclockwise direction; the X-ray generator 210 placed at the top of the arm frame 200 and emitting X-rays; the mammography plate 300 provided at the position corresponding to the X-ray generator 210 and obtaining an X-ray image of the breast of the target person; and the compression unit 400 placed between the X-ray generator 210 and the mammography plate 300 and moving vertically to compress the target part.

The mammography device further includes: the sensor unit 500 placed inside the mammography plate 300 and detecting whether the target person is present; and the control unit controlling the operation of the arm frame 200 on the basis of whether the target person is detected by the sensor unit 500.

Specifically, the sensor unit 500 includes: multiple sensors 510 placed on a front side 300a of the mammography plate 300 and detecting whether the target person is present; and a sensor substrate (PCB) 520 on which the multiple sensors 510 are arranged.

Figure 4:
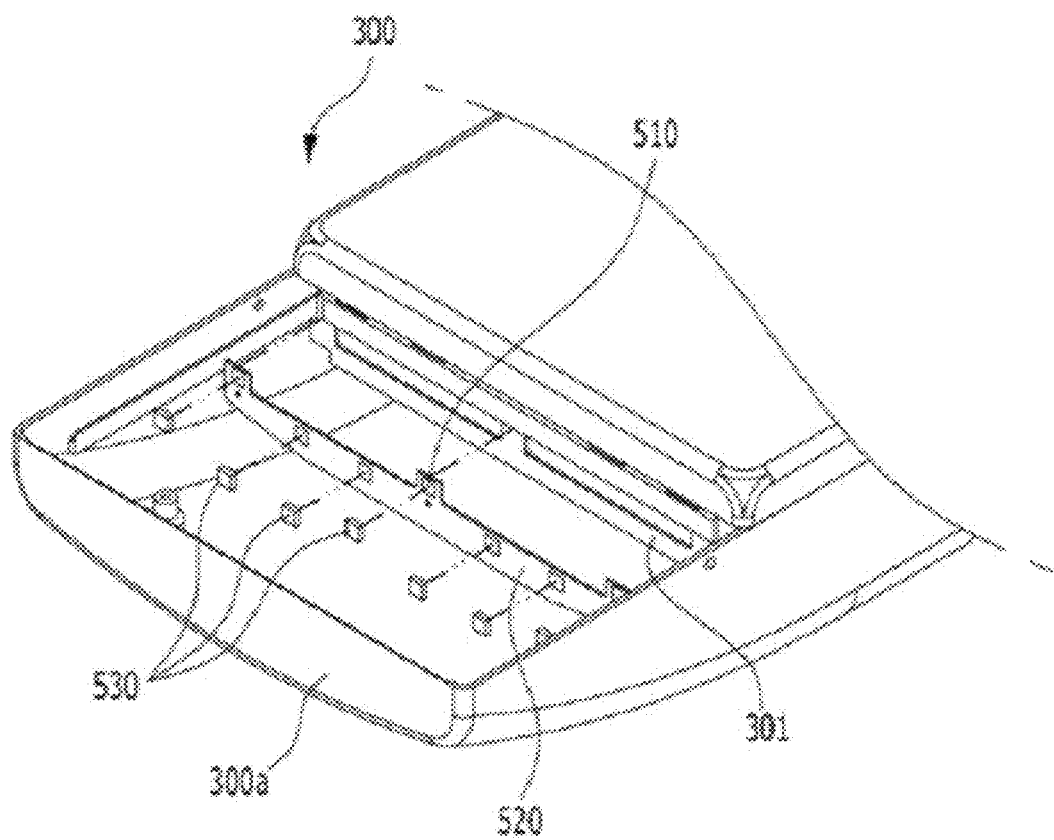
FIG. 4 is an exploded diagram illustrating a sensor unit positioned inside a mammography plate of the present invention.
Figure 5:
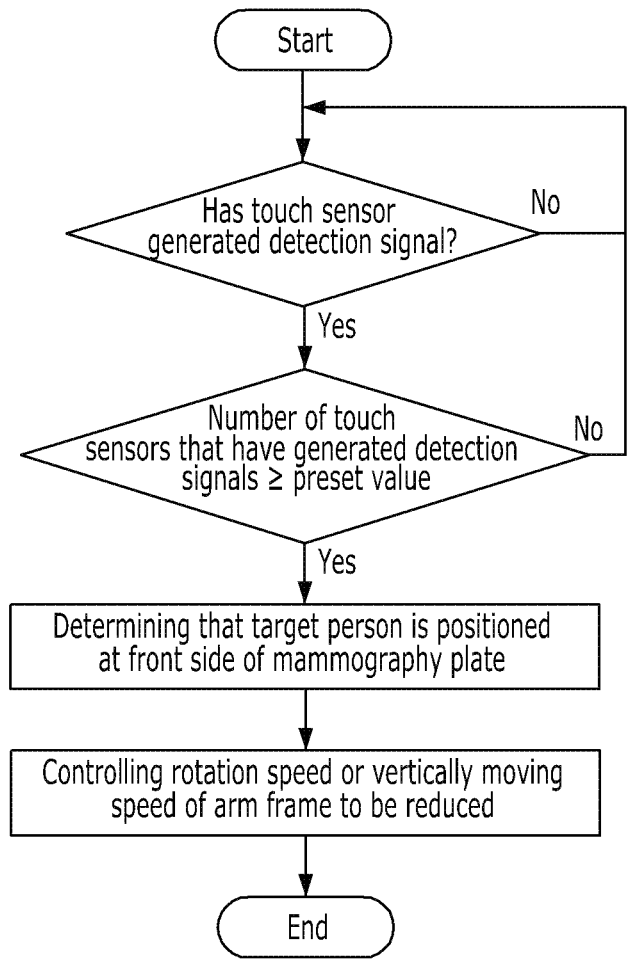
FIG. 5 is a flowchart illustrating an operation process of an arm frame of a mammography device of the present invention depending on whether a target person is present.

Moreover, the sensor substrate 520 on which the multiple sensors 510 are arranged is attached to a front side of an inner frame 301 that supports the X-ray detector 310 inside the mammography plate 300 as shown in FIGS. 2 to 4 above and such that the multiple sensors 510 are arranged on the front side 300a of the mammography plate 300 in an attached manner.

Here, the multiple sensors 510 may include an infrared sensor or an ultrasonic sensor, but it is desired that the multiple sensors 510 include a touch sensor capable of accurately and quickly detecting whether the target person is positioned at the front side 300a of the mammography plate.

Particularly, touch sensors includes various types of touch sensors such as an infrared touch sensor, a capacitive touch sensor, a resistive touch sensor, and the like. It is desired that the multiple sensors 510 include a capacitive touch sensor which has a fast response speed because touch is detected by sensing a change in capacitance.

However, it is merely a preferred embodiment that the multiple sensors 510 include a capacitive touch sensor, and other types of sensors may be used according to an embodiment if it is possible to check whether the target person is positioned at the front side 300a of the mammography plate 300.

The multiple sensors 510 which are capacitive touch sensors are arranged on the front side 300a of the mammography plate 300, detects a change in capacitance that occurs when the target person touches the fount side 300a of the mammography plate 300 for mammography, and detects whether the target person is present by generating a detection signal on the basis of the variation in capacitance.

The multiple sensors 510 are arranged on the sensor substrate 520 in any manner that is capable of detecting whether the target person is present. However, it is desired that the multiple sensors 510 are arranged at regular intervals on the sensor substrate 520 to recognize whether the target person is present, regardless of whether the body size (width) of the target person is wide or narrow.

However, it is merely an embodiment of the present invention that the multiple sensors 510 are arranged at regular intervals, so that the sensors 510 may be arranged arbitrarily without being spaced apart from each other.

Further, the multiple sensors 510 are regularly distributed over the front side 300a of the mammography plate as shown in FIGS. 3 and 4 so that whether the target person is present is accurately detected even when the target person leans to the left for LMLO mammography or even when the target person leans to the right for RMLO mammography.

As an example of the sensor unit 500 of the present invention shown in FIGS. 3 and 4, regarding the sensors 510, three sensors 510 are arranged on the upper portion and four sensors 510 are arranged on the lower portion so that via a total of seven sensors 510, whether the target person is present is detected in all regions of the left, the right, the upper portion, and the lower portion of the front side 300a of the mammography plate.

Here, the arrangement of the sensors 510 where the three sensors 510 are arranged on the upper portion and the four sensors 510 are arranged on the lower portion is merely an embodiment of the present invention and is not limited thereto. Seven or more sensors 510 may be arranged on the sensor substrate 520, or the sensors 510 may be arranged in one row without being divided into the upper portion and the lower portion or may be arranged in two or more rows.

Further, in order to prevent the operation speed of the arm frame 200 from reducing due to the malfunction of some of the multiple sensors 510 arranged on the front side 300a of the mammography plate even when the target person is not present at the front side 300a of the mammography plate, only when a detection signal is generated by a preset number of sensors 510 or more among the multiple sensors 510, the sensor unit 500 determines that the target person is positioned at the front side 300a of the mammography plate 300.

For example, in the case where the preset number is two, only when two or more sensors 510 generate the detection signals, the sensor unit 500 determines that the target person is positioned at the front side 300a of the mammography plate, and when only one sensor 510 generates the detection signal, the sensor unit 500 determines that a malfunction occurs and the target person is not positioned at the front side 300a of the mammography plate.

Here, it is merely an embodiment of the present invention that the preset number is two, and the preset number may be changed into three or four depending on the use environment.

Furthermore, in order to enhance the precision of detecting the target person by removing noise (electromagnetic interference) that occurs due to other electronic devices, the front side 300a of the mammography plate 300 is formed of an insulation material and the sensor unit 500 further includes multiple gaskets 530 arranged between the front side 300a of the mammography plate and the sensor substrate 520.

Here, the multiple gaskets 530 are arranged at the positions corresponding to the multiple sensors 510 arranged on the sensor substrate 520, and it is desired that the gasket is formed of a material having elasticity and conductivity.

Specifically, the entire regions of the multiple gaskets 530 are not necessarily formed of conducting polymer, but the surface of the multiple gaskets 530 which is in contact with the sensor 510 and the mammography plate 300 is formed of conducting polymer, such as polyethylene, polypyrrole, polythiophene, or the like, or the surface of the gasket 530 is coated with a conductive material such as the conducting polymer, whereby the portion being in contact with the sensor 510 and the mammography plate 300 has elasticity and conductivity.

However, this is merely an example, and the gasket 530 may be formed of any material having elasticity and conductivity according to an embodiment.

Next, the control unit is embedded in the body unit 100 and controls the operation of the arm frame 200 on the basis of the result (presence or absence of the target person) of the detection by the sensor unit 500.

Particularly, the control unit reduces the operation speed of the arm frame 200 when the sensor unit 500 detects that the target person is positioned at the front side 300a of the mammography plate.

Specifically, when the target person is detected by the sensor unit 500, the control unit reduces the rotation speed to a first set value or less while maintaining the angle at which the arm frame 200 rotates in a clockwise direction or in a counterclockwise direction.

Further, when the target person is detected by the sensor unit 500, the control unit reduces the speed at which the arm frame 200 moves vertically to a second set value or less while maintaining the distance at which the arm frame 200 moves vertically.

For example, when the target person is detected, the control unit reduces the rotation speed of the arm frame 200 into ⅕ or less of the rotation speed at which the arm frame 200 rotates in the case where the target person is not detected on the front side 300a of the mammography plate, and also reduces the vertically moving speed of the arm frame 200 into ⅕ or less of the vertically moving speed, whereby it is possible to prevent the target person from being injured by the operation of the arm frame 200 in the mammography process.

Here, the first set value and the second set value mean the rotation speed and the vertically moving speed of the arm frame 200 which are desired to be reduced compared to the rotation speed and the vertically moving speed of the arm frame 200 when the target person is not detected on the front side 300a of the mammography plate, for example, the speeds in a range of i) a speed of the arm frame 200 to finely adjust the position of the arm frame 200 for enhancement of the precision of mammography when the body of the target person is closely attached to the arm frame 200 for mammography to ii) a speed of the arm frame 200 in which the target person senses the rotation of the arm frame 200 and avoids the arm frame 200 when the target person does not assume the mammography posture and the arm frame 200 suddenly rotates.

Further, the reducing of the rotation speed and the vertically moving speed of the arm frame 200 into ⅕ or less is merely an embodiment of the present invention, and the first set value and the second set value are set differently depending on the implementation or use environment.

Finally, the effects of the mammography device of the present invention will be described with reference to FIGS. 6A to 7B.

Figure 6A:
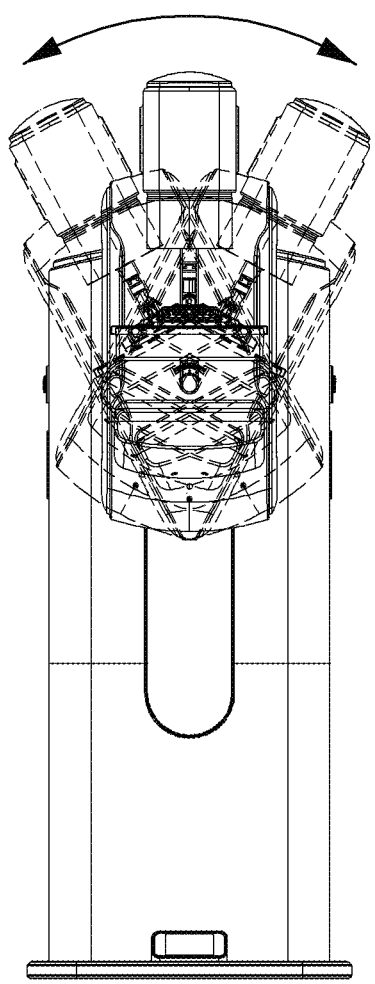
FIGS. 6A and 6B are diagrams illustrating an operation process of an arm frame of the conventional mammography device depending on whether a target person is present at a front side of a mammography plate.
Figure 6B:
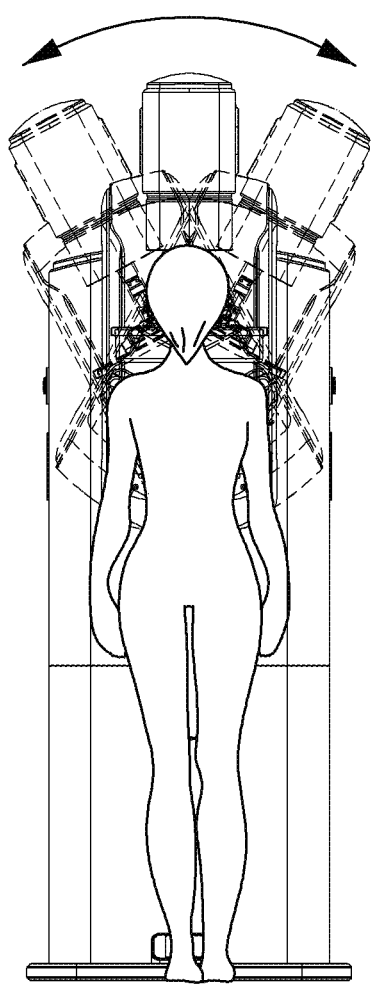
Figure 7A:
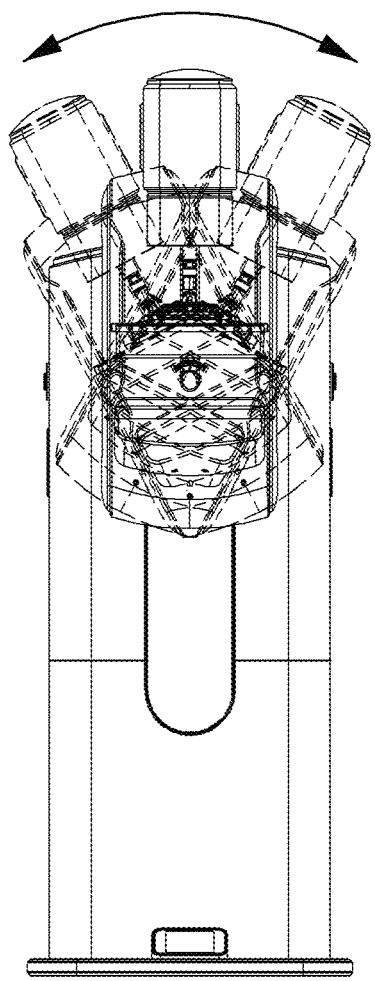
FIGS. 7A and 7B are diagrams illustrating an operation process of an arm frame of a mammography device of the present invention depending on whether a target person is present at a front side of a mammography plate.
Figure 7B:
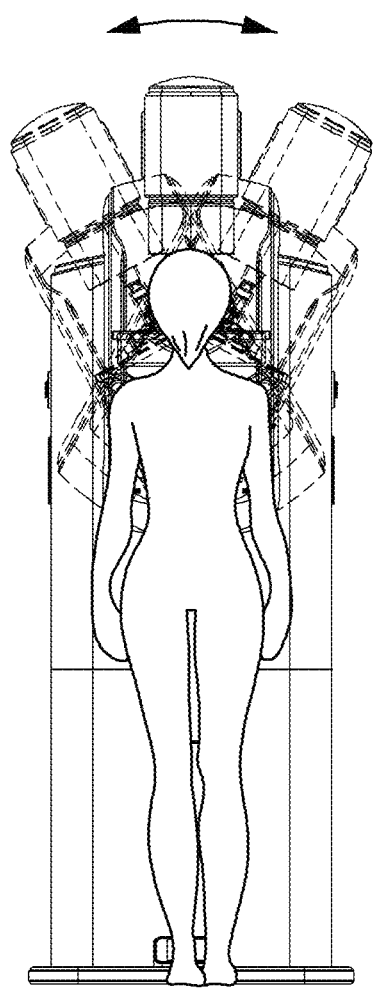

FIGS. 6A and 6B are diagrams illustrating an operation process of an arm frame of the conventional mammography device depending on whether a target person is present at a front side of a mammography plate. FIGS. 7A and 7B are diagrams illustrating an operation process of an arm frame of a mammography device of the present invention depending on whether a target person is present at a front side of a mammography plate.

As shown in FIGS. 6A and 6B, in the case of the conventional mammography device, regardless of whether the target person was positioned in front of the mammography device (specifically, the front side of the mammography plate), the rotation speed and the vertically moving speed of the arm frame remained constant, so that when the target person was positioned at the front side of the mammography plate, there was concern that the target person would be injured due to the operation of the arm frame.

Unlike the conventional mammography device, the mammography device according to an embodiment of the present invention further includes the sensor unit positioned in the front of the mammography plate and the control unit adjusting the operation speed of the arm frame on the basis of the result of the detection by the sensor unit. When the target person is not positioned at the front side of the mammography plate, the mammography device operates the arm frame in the same manner as the conventional mammography device, and when it is determined that the target person is positioned at the front side of the mammography plate, the mammography device reduces the operation speed of the arm frame as shown in FIG. 7B, whereby it is possible to prevent a safety accident that the target person is injured due to the rotation of the arm frame.

Further, the mammography device of the present invention slows down the operation speed of the arm frame when the target person is positioned at the front side of the mammography plate, so that the examiner is capable of more accurately adjusting the angle and the position of the arm frame. Accordingly, the mammography device of the present invention enhances convenience and accuracy in the examination process.

Although the exemplary embodiment and applications of the present invention have been described, the present invention is not limited to the above-described particular embodiment and applications, and is variously modified by those skilled in the art without departing the gist of the present invention claimed in the appended claims. The modifications should not be understood individually from the technical idea or perspective of the present invention.

Further, the terms used in the present invention are merely used to describe particular embodiments, and are not intended to limit the present invention. As used herein, the singular forms "a", "an", and "the" are intended to include the plural forms as well, unless the context clearly indicates otherwise.

The protection scope of the present invention should be defined by the accompanying claims, and the entire technical spirit of equivalents thereof should be construed as being included in the scope of the present invention.

What is claimed is:

1. A mammography device comprising:
    a body unit;
    an arm frame connected to the body unit and rotatable in a clockwise direction or in a counterclockwise direction;
    an X-ray generator placed at a top of the arm frame, and emitting X-rays;
    a mammography plate provided at a position corresponding to the X-ray generator for obtaining an X-ray image of a breast of a target person;
    an X-ray detector provided inside the mammography plate;
    a compression unit placed between the X-ray generator and the mammography plate and movable vertically to compress the breast;
    a sensor unit placed inside the mammography plate for detecting whether the target person is present; and
    a control unit controlling an operation of the arm frame on a basis of whether the target person is detected by the sensor unit;
    wherein the control unit reduces an operation speed of the arm frame when the target person is detected by the sensor unit such that a safety accident that may occur in an operation process of the arm frame is prevented.

2. The mammography device of claim 1, wherein the sensor unit comprises:
    multiple sensors placed on a front side of the mammography plate; and
    a sensor substrate on which the multiple sensors are arranged.

3. The mammography device of claim 2, wherein the multiple sensors comprise capacitive touch sensors.

4. The mammography device of claim 3, wherein the sensor unit further comprises:
    one or more gaskets arranged between the front side of the mammography plate and the sensor substrate.

5. The mammography device of claim 4, wherein the one or more gaskets are arranged at positions corresponding to the multiple sensors arranged on the sensor substrate.

6. The mammography device of claim 2, wherein the multiple sensors are arranged at regular intervals on the sensor substrate.

7. The mammography device of claim 2, wherein the sensor unit determines that the target person is positioned at the front side of the mammography plate when a detection signal is generated by a preset number of sensors among the multiple sensors.

8. The mammography device of claim 1, wherein the control unit reduces a rotation speed of the arm frame to a rotation speed equal to or less than a first set value when the target person is detected by the sensor unit.

9. The mammography device of claim 1, wherein the control unit reduces a vertically-moving speed of the arm frame to a vertically-moving speed equal to or less than a second set value when the target person is detected by the sensor unit.

* * * * *